United States Patent [19]
See

[11] Patent Number: 6,001,333
[45] Date of Patent: Dec. 14, 1999

[54] METHODS OF PREPARING MICRO ENCAPSULATED AGENTS FOR USE IN THE DETECTION OF TUMORS BY CT IMAGING

[76] Inventor: Jackie R. See, 541 Riveria Ct., Fullerton, Calif. 92635

[21] Appl. No.: 08/928,331

[22] Filed: Sep. 12, 1997

[51] Int. Cl.$^6$ .............................. A61K 49/04; B01J 13/02
[52] U.S. Cl. ........................... 424/9.4; 424/9.45; 264/4.1; 427/2.14; 427/213.3; 427/213.31
[58] Field of Search ..................................... 424/9.4, 9.45, 424/450, 489, 9.451, 9.452, 9.453, 499, 502; 264/4, 4.1, 4.3, 4.4, 9; 427/2.14, 213.3, 213.31; 428/402.2

[56] References Cited

U.S. PATENT DOCUMENTS

| | | | |
|---|---|---|---|
| 4,616,658 | 10/1986 | Shell et al. | 128/691 |
| 4,811,741 | 3/1989 | Shell et al. | 128/691 |
| 4,865,850 | 9/1989 | Shell et al. | 128/691 |
| 5,186,922 | 2/1993 | Shell et al. | 128/654 |
| 5,658,551 | 8/1997 | Schneidar et al. | 424/9.51 |
| 5,676,928 | 10/1997 | Klaveness et al. | 424/9.321 |
| 5,811,118 | 9/1998 | Ostro et al. | 424/450 |

FOREIGN PATENT DOCUMENTS

| | | | |
|---|---|---|---|
| 95/01777 | 1/1995 | WIPO | A61K 9/127 |

OTHER PUBLICATIONS

Seltzer, et al., "Biodistribution and Imaging Characteristics of Iotrolan–Carrying Interdigitation–Fusion Vesicles," *Investigative Radiology*, vol. 26, S169–S176, Nov. Supplement, 1991.

Caride, et al, "Relaxation enhancement using liposomes carrying paramagnetic species," *Magna Resonance Imaging* 2(2): 107–12, 1984.

Kanke, et al., "Interaction of Microspheres with Blood Constituents. III. Macrophage Phagocytosis of Various Types of Polymeric Drug Carriers," *Journal of Parenteral Science and Technology*, 42: 157–65, 1988.

Kanke, et al., "Interaction of microspheres with blood constituents II: Uptake of biodegradabe particles by macrophages," *Journal of Parenteral Science and Technolgy*, 40: 114–8, 1986.

Kanke, et al., "Interaction of microspheres with blood constituents:I. Uptake of polystyrene spheres by monocytes and granulocytes and effect on immune responsiveness of lymphocytes," *Journal of Parenteral Science and Technology*, 37 (6): 210–7, 1983.

Navon, et al., "Liposomes containing paramagnetic macromolecules as MRI contrast agents," *Magnetic Resonance in Medicine*, 3(6): 876–80, 1986.

See, et al., Successful Immunization of Mice Using Liposomes Containing Inactivated, Prototype Strains of All Six Types of Coxsackievirus Group B Viruses, *Vaccine Research*, vol. 6, No. 1, 1997.

Seltzer, et al., Contrast Material—carrying Liposomes: Biodistribution, Clearance, and Imaging Characteristics, *Radiology*, Mar. 1995.

Stark et al., "Hepatic metastases: randomized, controlled comparison of detection with MR Imaging and CT." *Radiology*, 165: 399–406, 1987.

Unger, et al., "Liposomal Gd–DTPA effect of encapsulation of enhancement of hepatoma model by MRI," *Magnetic Resonance Imaging*, 7: 417–23, 1989.

Unger, et al., Hepatic metastases: Liposomal Gd–DTPA—enhanced MR Imaging, *Radiology*, 171, 81–5, 1989.

*Primary Examiner*—Jose' G. Dees
*Assistant Examiner*—Michael G. Hartley
*Attorney, Agent, or Firm*—Koppel & Jacobs; Michael J. Ram

[57] ABSTRACT

X-ray contrast media encapsulated within 50 nm to 10 $\mu$m microspheres were shown to be a superior contrast agent for CT imaging of liver tumors. Use of the encapsulated agent resulted in significant improvement in the liver to tumor contrast ratio in CT images over prior art contrast media. The encapsulated media contrast also resulted in sustained contrast enhancement 1 hr after administration, providing the opportunity to use a lesser x-ray exposure in a single scan to discriminate cancerous tissue from normal surrounding tissue.

8 Claims, 7 Drawing Sheets

METHODS OF PREPARING MICRO ENCAPSULATED AGENTS FOR USE IN THE DETECTION OF TUMORS BY CT IMAGING

The invention relates to an improved method of preparing and using an x-ray contrast medium which results in improved contrast between body organs and parts thereof and, in particular, enhances the ability to visualize cancerous tumors in otherwise normal body organs. In particular, a contrast medium is encapsulated in liposomal spheres ranging from 50 nanometers to 10 microns in diameter which are preferentially retained in surrounding normal tissue but rapidly cleared from tumors.

BACKGROUND

Applicant has previously discovered that microspheres can be prepared from starches, fats, lipid particles, triglycerides, lipoproteins and free fatty acid lipids and these microspheres can be formed with radiopaque materials trapped within. These microspheres were beneficial in visualizing arterial vessels in the body. (U.S. Pat. Nos. 4,680,171 and 5,186,922).

However, there was no suggestion that those prior art microspheres were capable of preferential retention in different types of tissue, and, particularly normal tissue versus a cancerous tumor. Kanke et al. has shown that when polystyrene microspheres are introduced into the blood stream, spheres with diameters greater than 12 $\mu$m were predominantly localized in capillaries in the lungs. They have also shown by histologic studies that porous particles of polyglycolic acid (PGA) behave similar to the polystyrene sphere and individual 3- and 5-$\mu$m microspheres were found consistently in vascular channels, Kupffer cells, sinusoids of the liver and spleen, and within phagocytizing cells in the bone marrow. (Kanke, M., R. G. Geissler, D. Powell, A. Kaplan and P. P. DeLuca "Interaction of microspheres with blood constituents. III. Macrophage phagocytosis of various types of polymeric drug carriers." *Journal of Parenteral Science and Technology* 42: 157–65. (1988); Kanke, M., E. Morlier, R. Geissler, D. Powell, A. Kaplan and P. P. Deluca, "Interaction of microspheres with blood constituents II: Uptake of biodegradable particles by macrophages." *Journal of Parenteral Science and Technology* 40: 114–8 (1986); Kanke, M., I. Sniecinski and P. P. DeLuca, "Interaction of microspheres with blood constituents: I. Uptake of polystyrene spheres by monocytes and granulocytes and effect on immune responsiveness of lymphocytes." *J Parenter Sci Technol* 37(6): 210–7. (1983).) Others have shown that since hepatic tumors lack Kupffer cells and hepatocytes, unlike the liver, the use of liposomes with an average size of 100–200 nm results in the preferential accumulation of these particles in the liver tissue while being captured less by the tumor (Unger, E. C., P. MacDougall, P. Cullis and C. Tilcock, "Liposomal Gd-DTPA: effect of encapsulation on enhancement of hepatoma model by MRI." *Magnetic Resonance Imaging* 7:417–23. (1989).) However previous attempts to apply these teachings were limited either by the sizes of liposomes available (Seltzer, S. E., A. S. Janoff, M. Blau, D. F. Adams, S. R. Minchey and L. T. Boni "Biodistribution and imaging characteristics of iotrolan-carrying interdigitation-fusion vesicles." *Investigative Radiology* 26 Supl 1: S169–71; discussion S175–6 (1991)) or by the poor encapsulation efficiency or the tendency of the microcapsules to leak their contents of previous preparations. (Caride, V. J., H. D. Sostman, R. J. Winchell and J. C. Gore, "Relaxation enhancement using liposomes carrying paramagnetic species." *Magn Reson Imaging* 2(2): 107–12. (1984).)

Currently available contrast agents for x-ray CT imaging are not optimal for the detection of hepatic tumors. Meticulous use of intravenous liquid contrast material can increase the detection of individual metastatic lesions from 37% to 52%; however, no improvement in sensitivity for detecting abnormalities in normal patients has been achieved by meticulous liquid contrast CT imaging. (Stark, D. D., J. Wittenberg, R. J. Butch and J. T. Ferrucci, Jr., "Hepatic metastases: randomized, controlled comparison of detection with MR imaging and CT." *Radiology* 165: 399–406. (1987).)

Too many tumors are missed and there is an unacceptable level of false positives since less than 50% of metastatic liver cancers are detected with liquid contrast enhanced CT (Weyman, P. J., Lee, S. K. T., Helken, J. P. et al. "Prospective evaluation of hepatic metastasis: CT scanning, CT angiography, and MRI imaging" (abstr.) *Radiology,* 161, p. 206 (1986). Accordingly, there is a need for more specific contrast media and delivery techniques which will allow higher detection rates, more specificity and elimination of benign anomalies which occur in otherwise normal individuals.

SUMMARY

There is therefore a need for more effectual contrast agents that can be used in x-ray computed tomography (CT) particularly for the improved detection of hepatic tumors. It has been discovered that one can obtain improved results by exploiting the fact that the liver and hepatic tumors possess different vascular properties. This is accomplished by use of iodinated x-ray CT contrast agents encapsulated in liposomes embodying features of the invention. Larger amounts of such liposomes are captured in the liver tissue than in the tumor, thus increasing the liver to tumor contrast ratio.

The discovery of new effective CT contrast agents is dependent on several important biophysical properties possessed by liposomal contrast agents incorporating features of the inventions. First, the encapsulation efficiency of these liposomes, i.e., the amount of contrast agent per liposome, is 100% with 65% being iodinated contrast media and 35% other components of the liposome. The high encapsulation efficiency yields liposomes with a radiopacity, based on the amount of iodinated contrast plus media, that is equal to the radio-opacity of the free contrast agent used alone.

Secondly, it was found that the hepatic uptake of these liposomal contrast agents is greater than the uptake by the hepatic tumors. This increases the visibility of the tumor, which is x-ray transparent, within the opaque liver tissue following delivery of liposomal contrast agents when compared to the tumor visibility with intravenous delivery of the agent. The preferential disposition in the liver tissue depends on the specific size of the liposomes that are produced in accordance with the teaching herein.

It has now been found that iodinated contrast agents can be encapsulated in high dosages in lipid vesicles. When these lipid vesicles (liposome microspheres) are encapsulated with a high degree of efficiency the differential contrast between the normal tissue and tumor tissue, and in particular liver tissue and hepatic tumors, in CT imaging is significantly enhanced because the microspheres are preferentially entrapped in the normal liver tissue instead of the tumor.

DRAWINGS

These and other features, aspects and advantages of the present invention will become better understood with reference to the following description, appended claims, and accompanying drawings, where:

DETAILED DESCRIPTION OF PREFERRED EMBODIMENTS

Preparation of Animal Model

In order to prepare R3230 AC Fischer-344 rats for tumor fragment harvesting $1\times10^6$ R3230AC cells were subcutaneously (S.C.) injected into the left flank of the rat. Tumors grew to 1–2 cm in diameter in approximately 14 days at which point the tumors were removed from the rat and cut into cubes of 1~2 mm length on each side. The cubes were then stored in RPMI-1640 medium in an ice bath. The stored cubes of tumor were subsequently then used in growing additional R3230 AC tumors in the livers of tumor free Fischer-344 rats.

To grow the hepatic tumors rats were placed under anesthesia by intramuscular injection of Ketamine (87 mg/kg)+Rompun (13 mg/kg). The abdominal area was shaved and then cleaned with an alcohol pad. A vertical incision 2 cm in length reaching to peritoneum was made in the cleaned area and the liver was then accessed. A small hole was then created in the liver by using a fine sterilized tweezers and a tumor cube was placed therein. After the implantation, the liver was placed back in its original position in the abdominal cavity and the peritoneum was stitched with 5-0 silk followed by 5-0 or 4-0 suture. The R3230 AC tumors placed in the liver grew to 1.5~2 cm in diameter within 12~15 days at which time CT imaging studies were performed. After the imaging studies, the animals were sacrificed.

Preparation of Contrast Agent

A liposomal contrast agent incorporating features of the invention, referred to as Lipobrix™, was prepared by encapsulating Hexabrix® (loxaglate meglumine 39.3% and loxaglate sodium 19.6%) in the following the manner. 90 g of maltose was added to 450 mL of ultrapure water and mixed until completely dissolved. In a separate flask, 4.236 g of egg phosphatidylcholine (EPC) was mixed with 5 mL of 99.6% ethanol and stirred until the EPC was completely dissolved. 28 mg of BHT (Butylated hydroxytoluene) was then added to the aqueous maltose solution and the mixture was mixed again until completely dissolved. While continuously mixing the maltose/BHT solution the EPC-ethanol solution was added dropwise thereto at a rate of 2 drops per second.

450 mL Hexabrix®, containing 320 mg/mL organically bound iodine, was then added to the maltose/BHT//$H_2O$/EPC/Ethanol solution prepared as described above. The resultant mixture was stirred for 5 min. and then passed four times through a Microfluidizer 110Y at a pressure of 14–18K psi.

The Microfluidizer 110Y is a device manufactured by the Microfluidizer Corp. of Newton, Mass., used to form the liposome particles. These liposomes are formed by feeding, at high velocity and under pressure, a liquid containing the materials comprising the microcapsules, including the radiopaque material, through a small orifice into a temperature controlled chamber so that the liquid impinges on a wall therein causing the liquid stream to break into numerous discrete spheres which are then collected as a suspension in a non-dissolving carrier liquid.

The liposome suspension dispensed from the Microfluidizer was divided into 50 mL portions of the product each of which were placed into 100 cc vials. The contents of each vial was lyophilized as follows: 1) freeze to $-40°$ C., 2) place the product into a lyophilizer (Virtis Corporation) New York, N.Y. which is a steel lined vacuum chamber capable of maintaining $<100°$ C. temperature and <100 milli-Torr vacuum for up to 10 days with a gradual change of temperature and vacuum over pre-set periods and allow the product to reach $-20°$ C. or below, 3) activate the condenser portion of the lyophilizer and allow it to reach $-55°$ C. or below, 4) apply a vacuum to the lyophilizer and run in this configuration for 18–28 hours, 5) raise the temperature to $+25°$ C., and allow the product to reach $+20°$ C. or above, and 6) allow the lyophilizer to run for an additional 24 hours. At the end of this process 18 vials of a powdered, free flowing encapsulated agent (LIPOBRIX™) ready to be used in radiologic studies were recovered.

The resultant product was a powder composed of liposomal microspheres having diameters in the liquid state just prior to lyophilization from 5 nm to 10 $\mu$m with the distribution being a bell shaped curve with sizes being primarily 80% from 75 nm to 200 $\mu$m. The diameter of the microspheres, the relationship of different diameters within that distribution and the median diameter of the distribution curve can be varied by altering the pressure and/or flow rate of the microfluidizer prior to lyophilization, altering the stirring rate and surface tension of the liposomes, by changing their chemical composition and filtration through various filters of different pore sizes.

Figure 3:
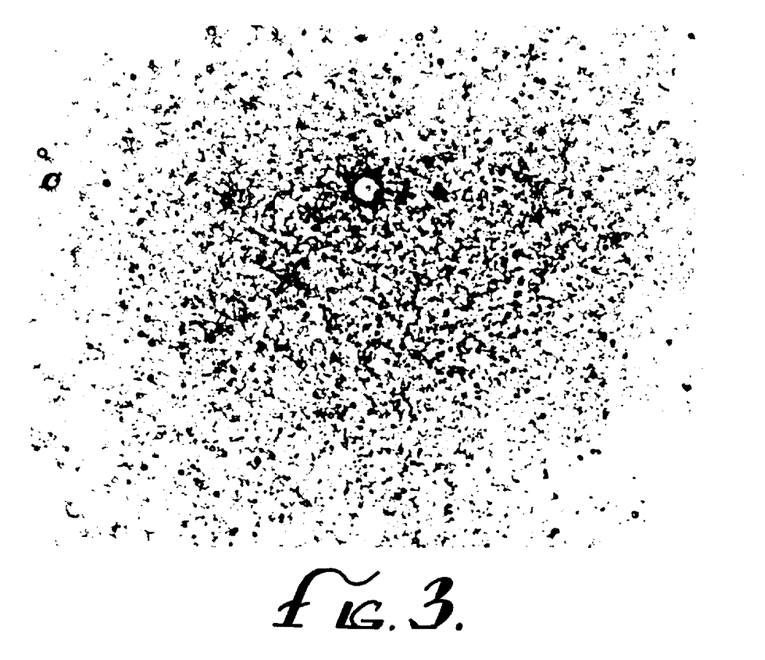
FIG. 3 and FIG. 4 are photomicrographs, at two different magnifications of a 150 nanometer (outer diameter) multilamellar lypholized liposome with encapsulated contrast media.
Figure 4:
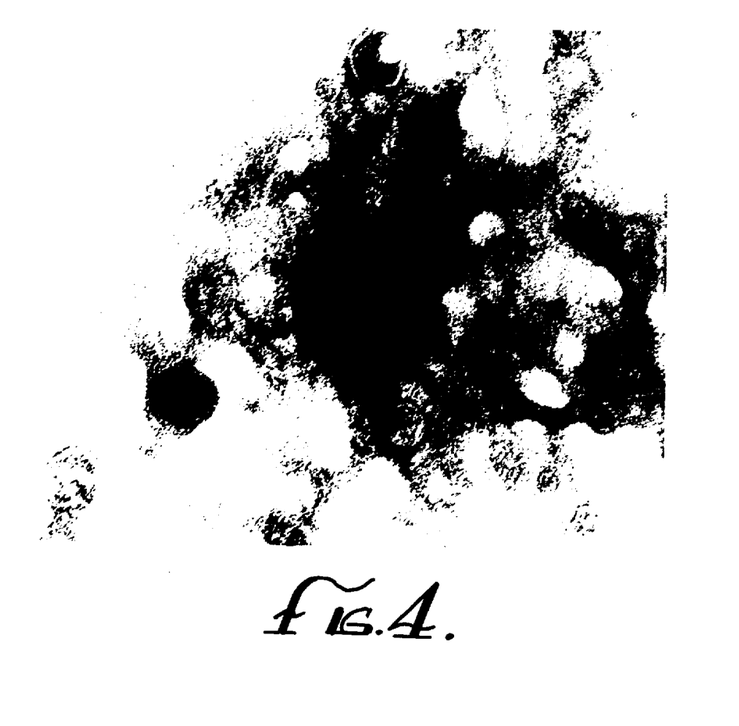

FIGS. 3 and 4 are photomicrographic showing a representative liposome. FIG. 3, at 6,000 magnification, clearly shows the presence of the radiopaque core. FIG. 4, at a magnification of 60,000, clearly shows the layered structure of the capsule wall.

Although the above procedure describes the liposomal encapsulation of an ionic contrast agent, other x-ray contrast agents could also be encapsulated by the same procedure.

CT Imaging of Tumor

CT imaging was performed on a GE 9800 scanner. The imaging parameters were: 120 kVp, 200 mA, and FOV=30 cm. Since the primary purpose was contrast differential, a reconstruction matrix of 320×320 with the soft tissue reconstruction filter was used. The slice thickness and scan time were 3 mm and 2 sec, respectively. In each study pairs of rats were used for the purpose of comparison of Hexabrix and Lipobrix. Each animal was anesthetized by injecting 50 mg/kg Ketamine (($\pm$)-2-(2–28 chlorophenyl)-2-(methylamino) cyclohexanone) mixed with 5 mg/kg Rompun (Zylazine) into the front limb. A 25 gauge butterfly cannula was then inserted into the tail vein for injection of contrast agent. The animal was then fastened to a paper board in the lateral decubitus position, and placed into the center of the scanning gantry. The location of the liver and tumor was determined from a scout view scan. A dynamic imaging sequence was then used to collect images before and after the injection of the contrast agent. The dynamic sequence was used to acquire a baseline comprising 4 images with a 28 sec interscan delay resulting in a time sampling of 30 sec per image before the injection of contrast agent (Phase I). After completion of the base line images one of the rats was injected with 2 mL/kg of Hexabrix in 5 ml of saline while the other was injected with 2 mL/kg of Lipobrix in 5 ml of saline as a bolus followed by a 5 mL of saline as a chaser. 30 images (each of which took 2 sec) with an interscan delay of 18 sec were collected immediately after the injection during the rapid passage phase of the contrast agents (Phase II) while an additional 30 images with an interscan delay of 1 min 58 sec were acquired during the clearance phase (Phase III) resulting in an overall scan time of 72 min and 64 images in total.

Although a dynamic CT image acquisition procedure was used in the current study, an advantage of the Lipobrix demonstrated by the study is that one can perform a single CT scan of the liver approximately 1 hr after intravenous injection, thus avoiding excessive radiation dose to the patients as well as eliminating the necessity for using more expensive dynamic CT scanners because of the unique, demonstrated retention of the liposomal contrast agent in the liver, as more fully discussed below.

Image Analysis

Signal intensities of tumor and liver were measured by placing a region of interest (ROI) over the respective areas and calculating the mean signal from each ROI. The process was repeated for all the images in the dynamic sequence to generate time-density curves. All the animals in the study underwent the same analysis. Because respiratory gating was not used the effect of respiratory motion was minimized by performing a 4-point time average during Phase I, 3-point time average during Phase II, and 5-point time averaging during Phase III. The percentage liver to tumor contrast ratio was calculated as a function of time as defined by, $$C(t) = \left[\frac{L(t) - T(t)}{L(t)}\right] \times 100 \quad (1)$$

where $C(t)$, $L(t)$, and $T(t)$ are percent contrast, liver signal, and tumor signal at time t, respectively. These quantities were measured as described above.

The percent contrast at time t=20 sec (peak value), 10 min, 30 min, and 70 min post injection were used to investigate the dynamics of each contrast agent as a function of time.

Figure 1:
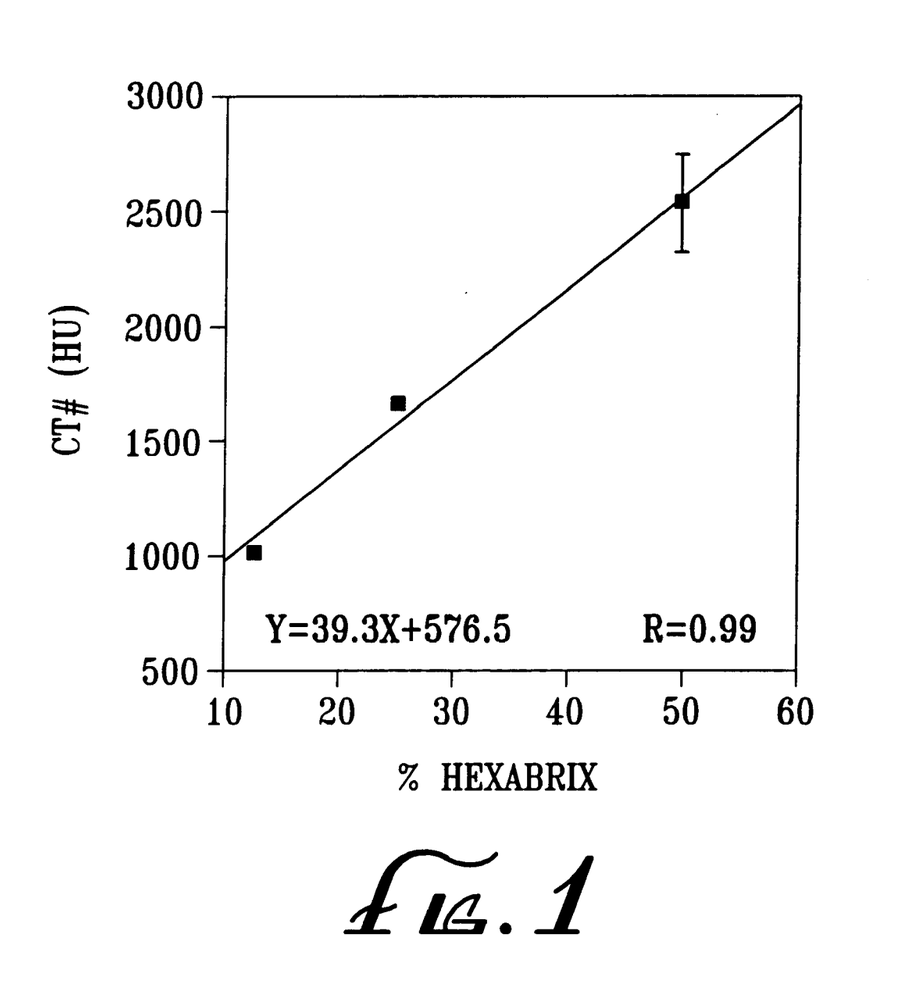
FIG. 1 is a calibration curve showing the CT number versus concentration for Hexabrix used to determine Lipobrix loading efficiency.

In order to compare the CT numbers of Lipobrix and Hexabrix several vials containing different dilutions of Hexabrix in 0.9% saline were prepared. The dilutions used for Hexabrix were: 12.5%, 25%, and 50%. The Lipobrix was likewise diluted by 50% to avoid any non-linearities at high Hounsfield numbers. The vials were placed into the scanner gantry and an axial slice was obtained through all four vials simultaneously. The image parameters were the same as set forth above with the exception that the slice thickness was 1 cm. The results are shown in FIG. 1. The average CT number corresponding to 50% Lipobrix was 2,338±83. The linear regression fit to the experimental data is also shown in the same figure. The CT number corresponding to 50% Lipobrix is 89.6% of the value, obtained by regression analysis, for 50% Hexabrix. This value corresponds to the loading efficiency of the liposomes. In other words, the CT number for the liposome encapsulated Hexabrix when adjusted for the weight of encapsulating materials is equal to that of the non-encapsulated Hexabrix. All tests were performed with equal amounts of contrast media injected.

Dynamic Studies

Figure 2A:
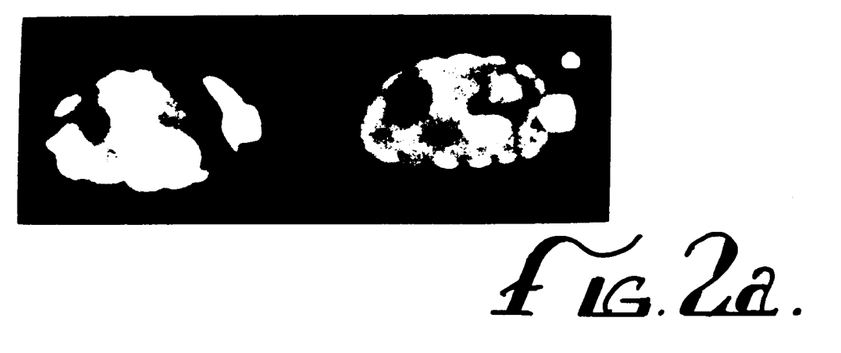
FIGS. 2a, 2b and 2c are photographic comparisons of transaxial CT images obtained through the livers of rats bearing R3230 AC at different times post-injection with Hexabrix (left) and Lipobrix (right).
Figure 2B:
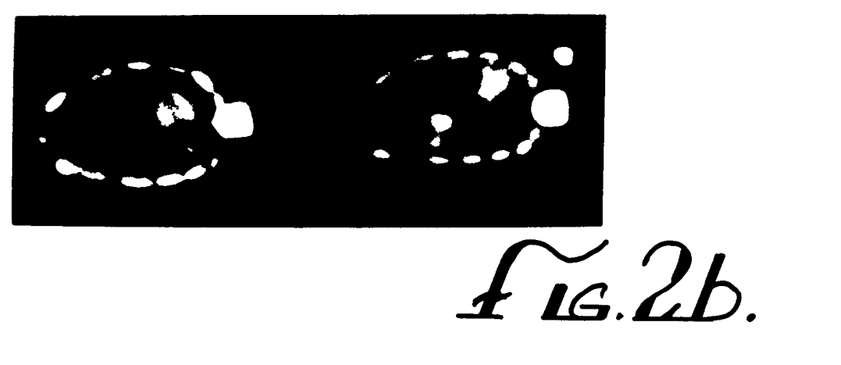
Figure 2C:
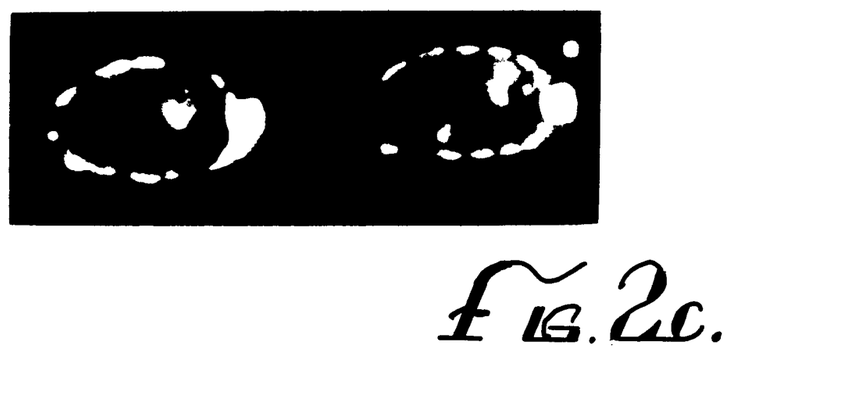

FIG. 2 shows a typical example of the dynamic images of rat livers obtained with the intravenous injection of Hexabrix and Lipobrix in two different rats having the R3230 AC hepatic tumor. The images are the results obtained at 20 sec (2a), 10 min (2b) and 68 min (2c) post injection. The images on the left correspond to 2 mL/kg Hexabrix and the images on the right are the Lipobrix images obtained with the same dose at the same time points.

Figure 5A:
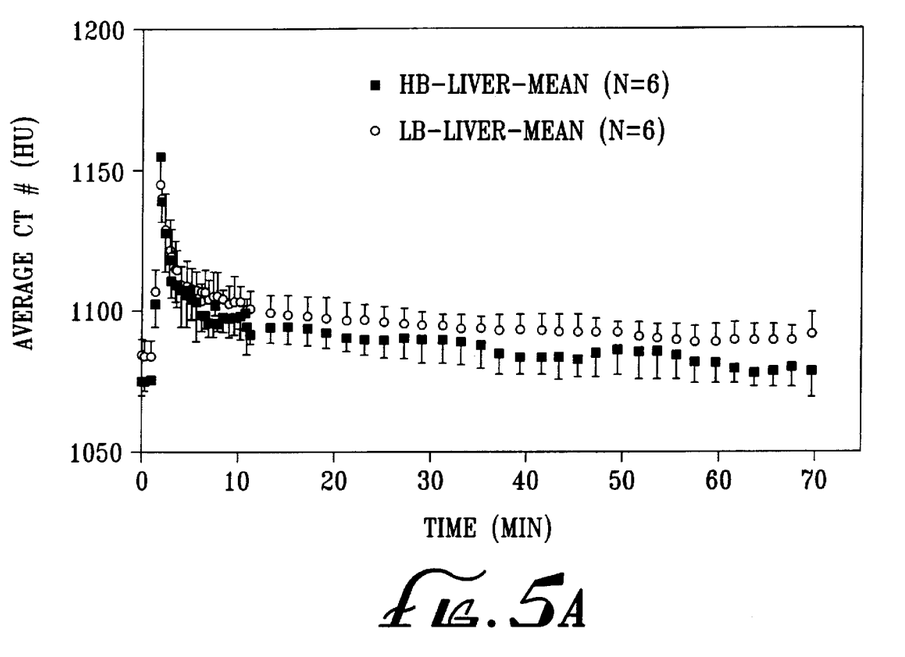
FIG. 5a and FIG. 5b are dynamic time density curves showing results of use of the Hexabrix (HB) and Lixabrix (LB) materials in rats.
Figure 5B:
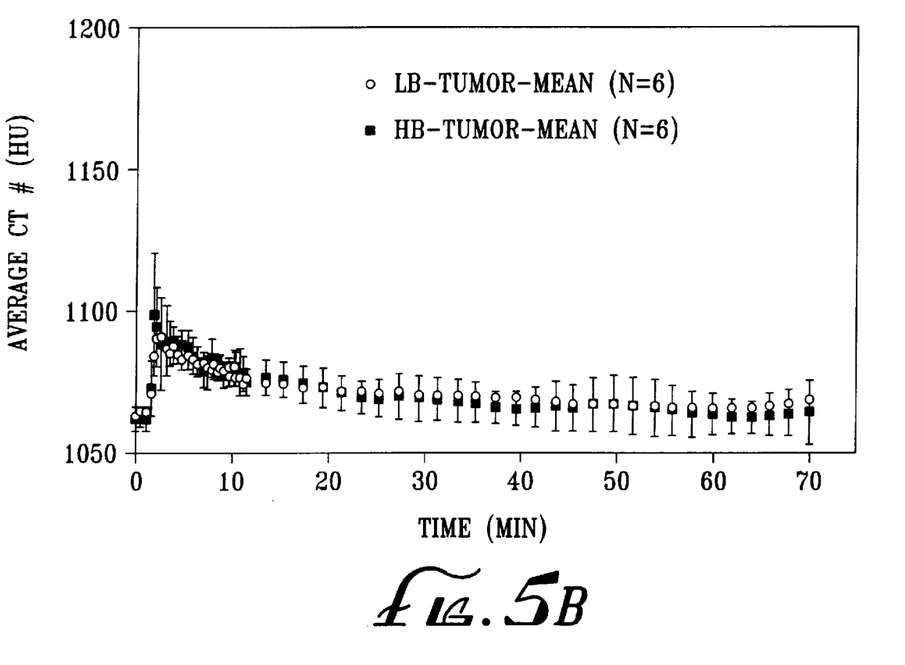

The dynamic time density curves averaged over 6 rats for each compound obtained from liver and tumor ROI's are shown in FIGS. 5a and 5b. The error bars corresponding to each measurement at a given time point are also shown for reference. FIG. 5a compares the liver signal with the tumor signal using the two compounds. FIG. 5b is similar to FIG. 5a except that in this case the measurements were performed on the tumor ROIs. The curves were obtained by averaging the measurements for each compound, each used in procedure performed on 6 rats.

Figure 6:
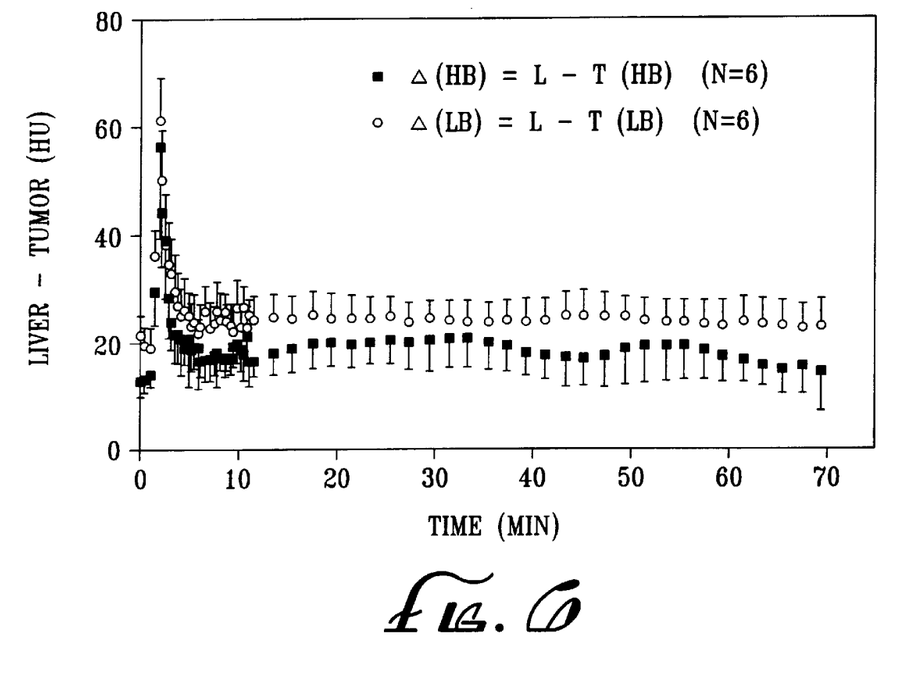
FIG. 6 is a graph showing differences between tumor and liver signals obtained as described for FIGS. 5a and 5b.

In order to study the enhancement of the liver image over the tumor image for each compound the average tumor signal was taken at a given time point and that value was subtracted from the corresponding liver signal. This is shown in FIG. 6. The curve labeled by Δ-HB(L-T) is the one obtained with Hexabrix. The other curve labeled as Δ-LB (L-T) was with Lipobrix.

Figure 7:
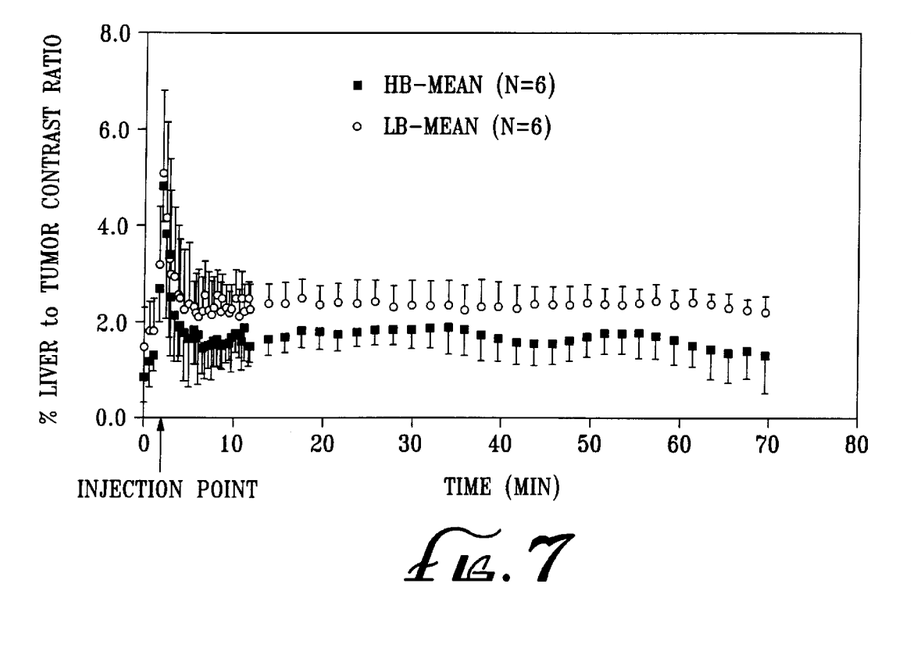
FIG. 7 is a graph using the data from FIGS. 5a and 5b showing the percent liver to tumor contrast.

The percent liver to tumor contrast ratio C(t) as defined in the above equation was computed using the date given in FIGS. 5a and 5b. The quantity is plotted against time in FIG. 7. The contrast agent was injected at t=2 min. The error bars for Lipobrix are shown in both directions whereas for Hexabrix only in the negative direction to reduce the crowding in the plot. Each point in the plot was obtained from an image from the dynamic CT sequence.

Figure 8:
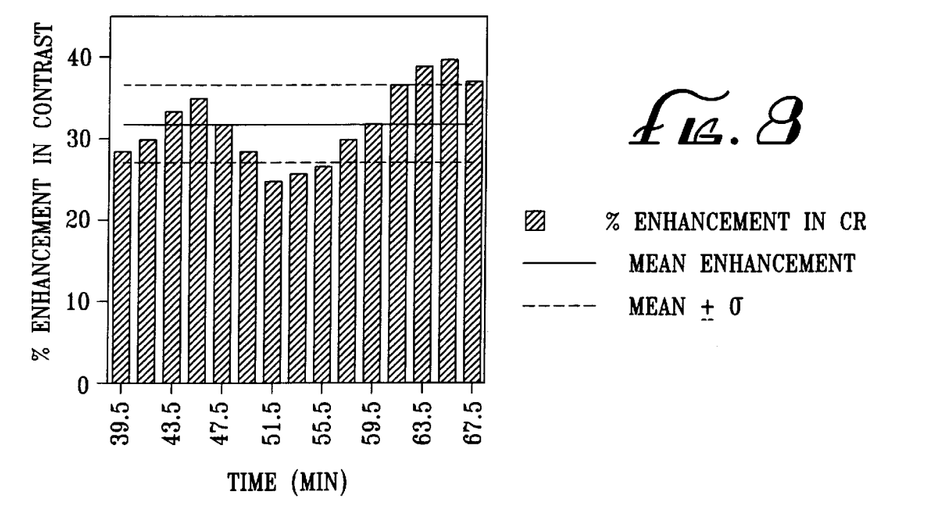
FIG. 8 is a graph showing the percent enhancement.

The difference between the Hexabrix and Lipobrix liver to tumor contrast ratios was evaluated by using student-t test for statistical significance. It was found that there was a highly significant difference (p<0.01) after t=38 minutes. In this time interval the contrast ratio obtained by Lipobrix was significantly higher than the one obtained by Hexabrix. Although the Lipobrix contrast ratio was higher than Hexabrix also for t<38 min, this was not found to be statistically significant. The percentage enhancement of Lipobrix contrast ratio compared to Hexabrix for t>38 min was then calculated. It was found that the percentage liver to tumor enhancement of Lipobrix compared to Hexabrix was 31.8±4.8% during this time interval. FIG. 8 is a bar graph showing the percentage enhancement during this time interval. The mean enhancement ±1 standard deviation are also shown in the same figure for reference.

The liver to tumor contrast ratios of Hexabrix and Lipobrix are given in Table 1 at different post-injection times.

TABLE 1

Liver to tumor contrast ratios at different times of Hexabrix and Lipobrix.

|  | Peak value | 10 min post-inj | 30 min post-inj | 72 min post-inj |
|---|---|---|---|---|
| Lipobrix (LB) | 7.5 | 2.9 | 2.7 | 2.6 |
| Hexabrix (HB) | 7.4 | 2.3 | 1.9 | 1.7 |
| LB/HB | 1.01 | 1.26 | 1.42 | 1.53 |

Due to the diameters of the contrast medium containing liposomes, the contrast medium was localized in the liver while not showing a substantial increase in the tumor signal. The encapsulation process described here yields liposomes with appropriate size and size distribution as well as high degree of encapsulation efficiency. The Liposomal CT contrast agent caused a greater enhancement in liver to tumor contrast ratio than the ionic CT contrast agent used alone. The increase in contrast between liver and hepatic tumor after intravenous injection of the liposomal CT contrast agent results from the rapid uptake of the liposomal contrast agent by normal liver (Kupffer cells and hepatocytes) compared to the implanted tumor in the liver which does not take up the liposomal CT contrast agent as efficiently, resulting in significant liver to tumor contrast ratios detected by CT imaging. It is believed that the normal liver hepatocyte uptake is the dominant factor since vascular enhancement diminishes in the images obtained after the 1 hr post-injection.

Microsphere diameters from 50 nm to 10μ are useful for performing the procedures described herein. The best images, i.e., the best contrast, are obtained with microspheres in the 100 nm to 5 μm range and agree with acceptable but less beneficial images outside the range. Superior images are obtained with a diameter range from 100 nm to 200 nm. Below 100 nm the microspheres are retained in increasing quantities in the microphage or reticular endothelium system. In the range of 200 nm to 5 microns the Kuppfer cell began to phagocytize the liposomes and above 5 μm the microspheres start to become entrapped in the capillaries of the lung. Either extreme (i.e. below 100 nm, or above 5 μm) reduces the amount of contrast media reaching the diagnostic site, for example the liver, reducing contrast between the liver and tumor. Dimensions and distributions are for liquid liposomes. However, freeze dried or lypholized materials have similar dimension and distributions.

Although the present invention has been described in considerable detail with reference to certain preferred versions and uses thereof, other versions and uses are possible. For example, while the present invention describes Hexabrix encapsulated by liposomes, the method is applicable to other available CT contrast agent. Furthermore, the possibility of detecting liver tumors with a single CT image at a point post-injection, for example 1 hour later, is also very desirable from the point of reduced radiation dose to the patient as well as the necessity for less sophisticated CT hardware making it more available in the developing countries. Also, while use for visualizing hepatic tumors in the liver is described, the Lipobrix product is usable for CT visualization of tumors in other body organs such as the kidney, lungs, heart, bone, brain, gut, endocrine glands, skin, fat, muscle, cartilage, breast, ovaries, pancreas, lymph nodes or for visualization using other x-ray techniques. Still further, the technique described herein can be used for encapsulating other media used in other diagnostic techniques such as radioactive materials for nuclear scans, phosphorescent materials used in optical visualization techniques, magnetic resonance imaging agents, or to entrap molecular targets, growth factors, and tumor-killing agents which are coupled to tumor specific antibodies. Therefore, the spirit and scope of the appended claims should not be limited to the description of the preferred versions contained herein.

What is claimed is:

1. A method of preparing improved microcapsules for delivery of a substance encapsulated therein to normal tissue cells in mammalian body comprising:
   a. mixing maltose with water in the ratio of about 20 grams maltose to 100 ml of water and stirring until the maltose is dissolved to form an aqueous solution,
   b. mixing egg phosphatidylcholine with 99.6% ethanol in the ratio of about 4.2 g of the egg phosphatidylcholine to 5 ml of the ethanol and stirring until dissolved to form an alcohol solution,
   c. adding BHT to the aqueous solution in the ratio of about 6.2 mg BHT to 20 g maltose,
   d. adding the alcohol solution to the aqueous solution in a dropwise manner with continuous mixing until a solution is obtained which contains 5 ml ethanol for each 450 ml of water to form an encapsulating solution,
   e. stirring the substance to be encapsulated into the encapsulating solution,
   f. passing the mixture from step e above through a microfluidizing device to form a clear solution and
   g. lyphilizing the mixture from step f,
   about 100% of the substance being encapsulated in the microcapsules.

2. The method of claim 1 wherein step g is accomplished by cooling the clear solution to −40° C., placing the cooled solution into a lyophilizer, maintaining the solution below −20° C., applying a vacuum to the solution, said vacuum maintained for at least 18 hours, allowing the contents of the lyophilizer to reach 20° C. and maintaining the contents of the lyophilizer under vacuum for at least 24 hours, the resultant product comprising microcapsules having a diameter from about 50 nm to about 10 μm in diameter.

3. The method of claim 2 wherein the microcapsules have a diameter from about 100 nm to about 5 μm in diameter.

4. The method of claim 1 wherein the substance encapsulated is a radiopaque material.

5. The method of claim 4 wherein the radiopaque material is 39.3% loxaglate meglumine in combination with 19.6% loxaglate sodium.

6. The method of claim 5 wherein the microcapsules have a diameter from about 100 nm to about 5 μm in diameter and contain in excess of 100 ml of radiopaque material per gram of egg phosphatidylcholine.

7. The method of claim 4 wherein the microcapsules comprise about 89% by weight of the radiopaque material.

8. The method of claim 2 wherein the microcapsules have a diameter of 5 nm to 10 μm.

* * * * *